US00PP10324P

United States Patent [19]

Moore

[11] Patent Number: Plant 10,324

[45] Date of Patent: Apr. 14, 1998

[54] HYBRID TEA ROSE PLANT NAMED 'MORJOYBON'

[75] Inventor: Ralph S. Moore, Visalia, Calif.

[73] Assignee: Spring Hill Nurseries Co., Tipp City, Ohio

[21] Appl. No.: 707,324

[22] Filed: Sep. 3, 1996

[51] Int. Cl.[6] ..... A01H 5/00

[52] U.S. Cl. ..... Plt./16

[58] Field of Search ..... Plt./11, 15, 16, Plt./18

[56] References Cited

U.S. PATENT DOCUMENTS

P.P. 7,055 11/1989 Moore ..... Plt./10.1
P.P. 9,807 2/1997 van der Meer ..... Plt./18
P.P. 9,808 2/1997 van der Meer ..... Plt./18

*Primary Examiner*—Howard J. Locker
*Attorney, Agent, or Firm*—Christie, Parker & Hale, LLP

[57] ABSTRACT

A new variety of hybrid tea rose plant producing apricot blend flowers.

1 Drawing Sheet

SUMMARY OF THE INVENTION

The present invention relates to a new and distinct variety of rose of the hybrid tea rose class which was originated by my crossing as seed parent the variety known as 'Morjoye' (U.S. Plant No. 7,055) and as pollen parent the variety known as 'Bon Silene.' The varietal denomination of this new rose is 'Morjoybon.'

Among the novel characteristics possessed by this new variety which distinguishes it from its parents are its floriferousness and apricot blend flowers. The plant grows and blooms well both in the greenhouse and outdoors and is good for garden decoration. Plants of the new variety are vigorous and have a rounded to upright growth shape. Garden plants flower throughout growing season.

Asexual reproduction of the new variety by budding and by vegetative cuttings as performed in Visalia, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression of the variety herein described, including colors, may vary depending upon growing conditions, such as climate, soil, and environmental conditions.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. General terms such as average, normal, ordinary, medium, etc. are used in their normal sense and the characteristics so described are not considered distinguishing.

Parentage: Seedling.

*Seed parent.*—'Morjoye', a miniature rose

*Pollen parent.*—'Bon Silane', an old Tea rose (1839).

Class: Hybrid tea.

The following information is from observations made of specimens grown in Visalia, Calif.

FLOWER

Blooming habit: Continuous.

A. Bud:

(1) *Size.*—Medium.

(2) *Form.*—Pointed, with several small foliaceous appendages on surface of the bud extending beyond tip of bud to more than ½ of its length.

(3) *Color.*—As sepals divide, bud color is near 16A (outdoors), sometimes tinged with bronze.

(4) *Sepals.*—Spear shaped; recurved.

(5) *Peduncle.*—Length: About 5 to 8 cm. Aspect: Generally straight, nearly smooth. Strength: Sturdy, erect, slender. Color: Green with purple-bronze coloration outdoors.

B. Bloom:

(1) *Size.*—About 7 to 9 cm.

(2) *Borne.*—Usually singly, sometimes in small clusters; opens well in all weather conditions; flower stem length of mature plants grown outdoors is about 35 to 60 cm.

(3) *Form.*—High centered at first, becoming flat to rounded with petals rolled loosely downward. Fully open blooms usually show stamens.

(4) *Petalage.*—Number of petals under normal conditions—about 60 or more, plus several small petaloids.

(5) *Color.*—Outer petals—Top surface—near near 32D blending into yellow at base (in plastic greenhouses). Undersurface—near 32D blending into yellow at base. Intermediate petals—similar to outer petals. General tonality from a distance—soft apricot blending into lighter shades.

(6) *Color change.*—After about three days, color of open bloom is similar to newly open flower but lighter and less bright. Flower color becomes progressively lighter as flowers age.

(7) *Fragrance.*—Old garden rose fragrance.

C. Petals:

(1) *Texture.*—Thick.

(2) *Appearance.*—Inside satiny; outside satiny.

(3) *Form.*—Broad lanceolate with rounded tip.

(4) *Arrangement.*—Imbricated.

(5) *Petaloids in center.*—Several small petaloids.

(6) *Persistence.*—Petals drop off cleanly.

(7) *Lasting quality.*—On potted plant about 4 to 6 or more days; about 4 to 5 days in vase after cutting.

REPRODUCTIVE ORGANS

A. Stamens, filaments and anthers:

*Arrangement.*—Stamens regularly arranged about pistils.

*Filaments.*—Short, yellow.

*Anthers.*—Well formed, yellow.

*Pollen.*—Some.

B. Styles: Long, yellowish, bunched.

C. Ovaries: Enclosed in calyx.

D. Hips: Usually none, no seeds.

PLANT

A. Form: Upright, much branched.

B. Growth: Very vigorous, about 122 cm in height and about 90 to 120 cm in width.

Foliage:

(1) *Leaves.*—Compound 5, sometimes 3 and 7, leaflets; terminal leaflet is about 5 to 7.5 cm long by about 3.5 to 5 cm wide.

(2) *Quantity.*—Abundant.

(3) *Leaflets.*—Broad lanceolate, apex acute, base rounded, semi-glossy top and matte undersurface.

(4) *Color.*—New foliage: Medium green, sometimes reddish tint. Old foliage: Medium green but can be as dark as near 147A on top side and near 147C on under side.

(5) *Rachis.*—Medium length, upper side smooth, grooved, underside may have several small prickles.

(6) *Stipules and petioles.*—Stipules — medium to short length, medium width, medium to short narrow points that usually turn out about 45° or less; petioles — medium length, medium to broad width, short upward prickly points, medium green with yellowish green midsection.

(7) *Edge.*—Serrated.

(8) *Serration.*—Regular.

(9) *Resistance to disease.*—Resistant to mildew, rust and blackspot.

D. Main stems: Medium green, near 134B, with bronze tint.

E. Thorns:

(1) *Thorns.*—Varying size and length, usually straight to slightly downward, brown, few or no hairs.

Winter hardiness: Completely winter hardy in Visalia, Calif.

I claim:

1. A new and distinct variety of rose plant of the hybrid tea rose class, substantially as shown and described.

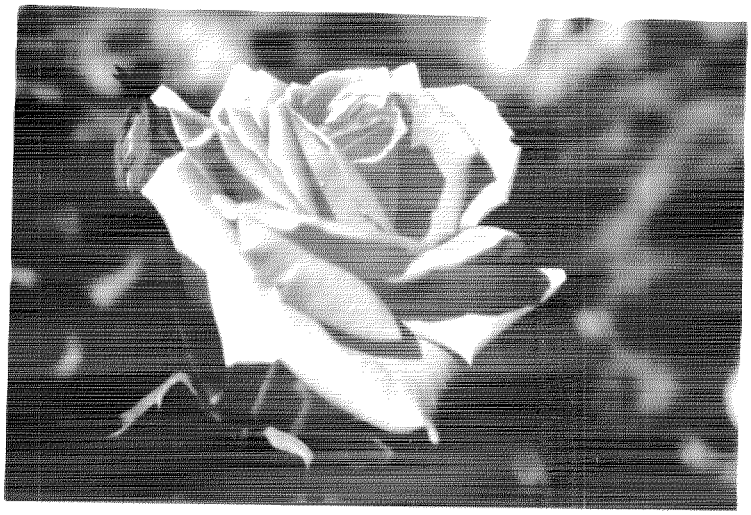

* * * * *